(12) United States Patent
Udagawa et al.

(10) Patent No.: US 9,579,061 B2
(45) Date of Patent: Feb. 28, 2017

(54) HOLDER SET AND BRAIN FUNCTION MEASURING DEVICE USING SAME

(75) Inventors: Haruhide Udagawa, Kyoto (JP); Yoshihiro Inoue, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 524 days.

(21) Appl. No.: 14/005,824

(22) PCT Filed: Apr. 11, 2011

(86) PCT No.: PCT/JP2011/059016
§ 371 (c)(1),
(2), (4) Date: Sep. 18, 2013

(87) PCT Pub. No.: WO2012/140719
PCT Pub. Date: Oct. 18, 2012

(65) Prior Publication Data
US 2014/0018640 A1    Jan. 16, 2014

(51) Int. Cl.
*A61B 5/1455*    (2006.01)
*A61B 5/00*    (2006.01)
(Continued)

(52) U.S. Cl.
CPC .......... *A61B 5/6814* (2013.01); *A61B 5/0042* (2013.01); *A61B 5/0059* (2013.01);
(Continued)

(58) Field of Classification Search
CPC .............. A61B 5/0059; A61B 5/14552; A61B 5/14553; A61B 5/6814; A61B 2562/0233; A61B 2562/046; A61B 5/0478
See application file for complete search history.

(56) References Cited

U.S. PATENT DOCUMENTS 6,161,030 A * 12/2000 Levendowski ...... A61B 5/0478
                                                  600/383
6,574,513 B1 * 6/2003 Collura ................ A61B 5/0478
                                                  600/383
(Continued)

FOREIGN PATENT DOCUMENTS

JP    2001-337033    12/2001
JP    2006-223503    8/2006
(Continued)

OTHER PUBLICATIONS

"International Search Report (Form PCT/ISA/210)", mailed on Jul. 19, 2011, with English translation thereof, p. 1-p. 4.
(Continued)

*Primary Examiner* — Eric Winakur
(74) *Attorney, Agent, or Firm* — Jianq Chyun IP Office (57) ABSTRACT

This holder set is provided with: an optical bioinstrumentation holder which has at least two probe mounting units into which are inserted light-transmitting probes which irradiate light from the tip, or light-receiving probes which receive light from the tip, and which is mounted on the subject's head; and a electroencephalograph holder which has at least one electrode mounting unit into which an EEG electrode is inserted which detects the potential difference with a reference electrode. This optical bioinstrumentation holder is provided with a linear trunk unit extending in a first direction, and at least two linear branches extending in a second direction different from the first direction, and the electroencephalograph holder is provided with a linear trunk unit extending in a first direction, and at least one linear branch extending in the direction opposite to said second direction.

1 Claim, 9 Drawing Sheets

(51) Int. Cl.
*A61B 5/0476* (2006.01)
*A61B 5/0478* (2006.01)

(52) U.S. Cl.
CPC .......... *A61B 5/0476* (2013.01); *A61B 5/0478* (2013.01); *A61B 5/6803* (2013.01); *A61B 5/72* (2013.01); *A61B 5/742* (2013.01); *A61B 5/7475* (2013.01); *A61B 2562/0238* (2013.01); *A61B 2562/066* (2013.01)

(56) References Cited

U.S. PATENT DOCUMENTS

| | | | |
|---|---|---|---|
| 7,139,600 B2* | 11/2006 | Maki .................... | A61B 5/0059 600/344 |
| 8,396,525 B2* | 3/2013 | Ishikawa ............ | A61B 5/14553 600/310 |
| 8,527,035 B2* | 9/2013 | Diamond ........... | A61B 5/14552 600/473 |
| 2004/0082862 A1* | 4/2004 | Chance ................ | A61B 5/0059 600/473 |

FOREIGN PATENT DOCUMENTS

| | | |
|---|---|---|
| WO | 2011/114479 | 9/2011 |
| WO | 2012/008047 | 1/2012 |

OTHER PUBLICATIONS

Gary Strangman et al., "Factors affecting the accuracy of near-infrared spectroscopy concentration calculations for focal changes in oxygenation parameters," NeuroImage 18, Apr. 2003, pp. 865-879.

* cited by examiner

HOLDER SET AND BRAIN FUNCTION MEASURING DEVICE USING SAME

CROSS-REFERENCE TO RELATED APPLICATIONS

This application is a 371 application of an international PCT application serial no. PCT/JP2011/059016, file on Apr. 11, 2011. The entirety of the above-mentioned patent application is hereby incorporated by reference herein and made a part of this specification.

TECHNICAL FIELD

The invention is related to a holder set and a brain function measuring device using the same, and particularly to a holder set capable of executing measurements by an optical bioinstrumentation device and by an electroencephalograph (EEG) at the same time and to a brain function measuring device using the same.

BACKGROUND ART

In recent years, optical brain-function imaging devices (light measuring devices) configured to perform measurements simply and noninvasively using light have been developed in order to observe brain activities. In such optical brain-function imaging devices, near-infrared light of three different wavelengths $\lambda 1$, $\lambda 2$ and $\lambda 3$ (e.g. 780 nm, 805 nm and 830 nm) is irradiated by a light-transmitting probe arranged on a surface of a subject's head to the brain, and intensity (information on an amount of received light) $A(\lambda 1)$, $A(\lambda 2)$ and $A(\lambda 3)$ of the near-infrared light of the respective wavelengths $\lambda 1$, $\lambda 2$ and $\lambda 3$ released from the brain are respectively detected by a light-receiving probe arranged on the surface of the head.

Then, from the information on the amount of light received $A(\lambda 1)$, $A(\lambda 2)$ and $A(\lambda 3)$ obtained in above manner, in order to obtain the product [oxyHb] of oxyhemoglobin concentration in cerebral blood flow and optical path length as well as the product [deoxyHb] of deoxyhemoglobin concentration and optical path length, simultaneous equations as shown in relational expressions (1), (2) and (3) are prepared using the Modified Beer Lambert Law, for example, and the simultaneous equations are solved (see Non-Patent Literature 1, for example). Furthermore, the total product ([oxyHb]+[deoxyHb]) of hemoglobin concentration and optical path length is calculated from the product [oxyHb] of the oxyhemoglobin concentration and the optical path length as well as the product [deoxyHb] of the deoxyhemoglobin concentration and the optical path length.

$$A(\lambda_1)=E_O(\lambda_1)\times[\text{oxyHb}]+E_d(\lambda_1)\times[\text{deoxyHb}] \quad (1)$$

$$A(\lambda_2)=E_O(\lambda_2)\times[\text{oxyHb}]+E_d(\lambda_2)\times[\text{deoxyHb}] \quad (2)$$

$$A(\lambda_3)=E_O(\lambda_3)\times[\text{oxyHb}]+E_d(\lambda_3)\times[\text{deoxyHb}] \quad (3)$$

Furthermore, $E_O(\lambda m)$ is a light absorbance coefficient of oxyhemoglobin for light of a wavelength $\lambda m$, and $E_d(\lambda m)$ is a light absorbance coefficient of deoxyhemoglobin for light of the wavelength $\lambda m$.

Figure 7:
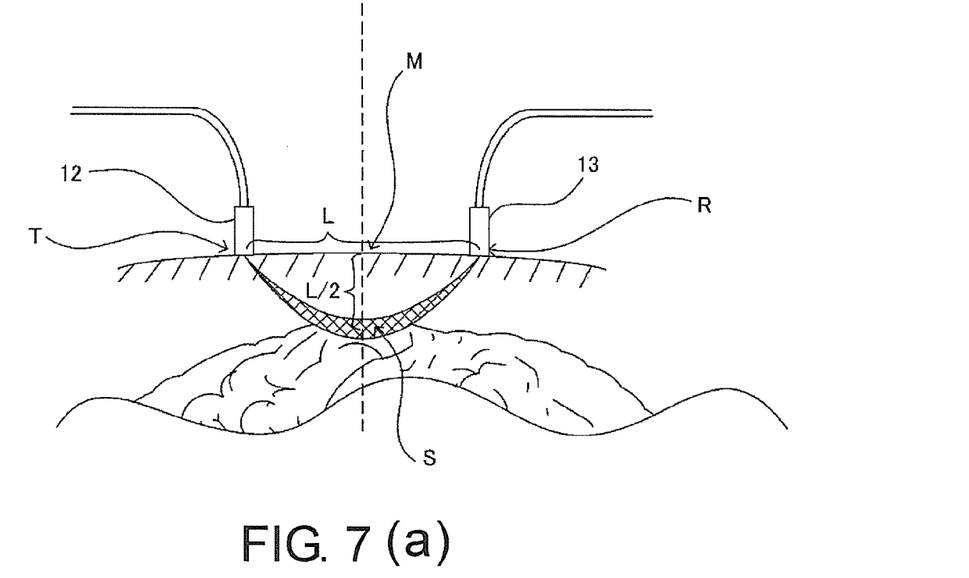
FIGS. 7(a) and 7(b) are diagrams showing a relationship between a portion to be measured and one pair of light-transmitting probe and light-receiving probe.

Here, a relationship between a portion to be measured and a distance (channel) between the light-transmitting probe and the light-receiving probe is described. FIG. 7(a) is a cross-sectional diagram showing the relationship between the portion to be measured and one pair of light-transmitting probe and light-receiving probe, and FIG. 7(b) is a plan diagram of FIG. 7(a).

A light-transmitting probe 12 is pressed against a light-transmitting point T on the surface of the subject's head, and a light-receiving probe 13 is pressed against a light-receiving point R on the surface of the subject's head. Then, light is irradiated from the light-transmitting probe 12, and light released from the surface of the head enters the light-receiving probe 13. Currently, of the light that has been irradiated from the light-transmitting point T on the surface of the head, the light that has passed through a banana-shaped area (area to be measured) reaches the light-receiving point R on the surface of the head. Accordingly, the information on the amount of light received $A(\lambda 1)$, $A(\lambda 2)$ and $A(\lambda 3)$ related to a portion to be measured S of the subject at a depth L/2, which is half of the distance along the line connecting the light-transmitting point T and the light receiving-point R along the surface of the subject's head from the middle point M of the line L connecting the light-transmitting point T and the light-receiving point R along the surface of the subject's head, is particularly obtained from among the area to be measured.

In addition, in the optical brain-function imaging devices, a near-infrared spectrometer, for example, is used in order to measure respectively the product [oxyHb] of the oxyhemoglobin concentration and optical path length, the product [deoxyHb] of the deoxyhemoglobin concentration and optical path length, and the product ([oxyHb]+[deoxyHb]) of the total hemoglobin concentration and optical path length related to a plurality of portions to be measured in the brain (see Patent Document 1, for example).

Figure 8:
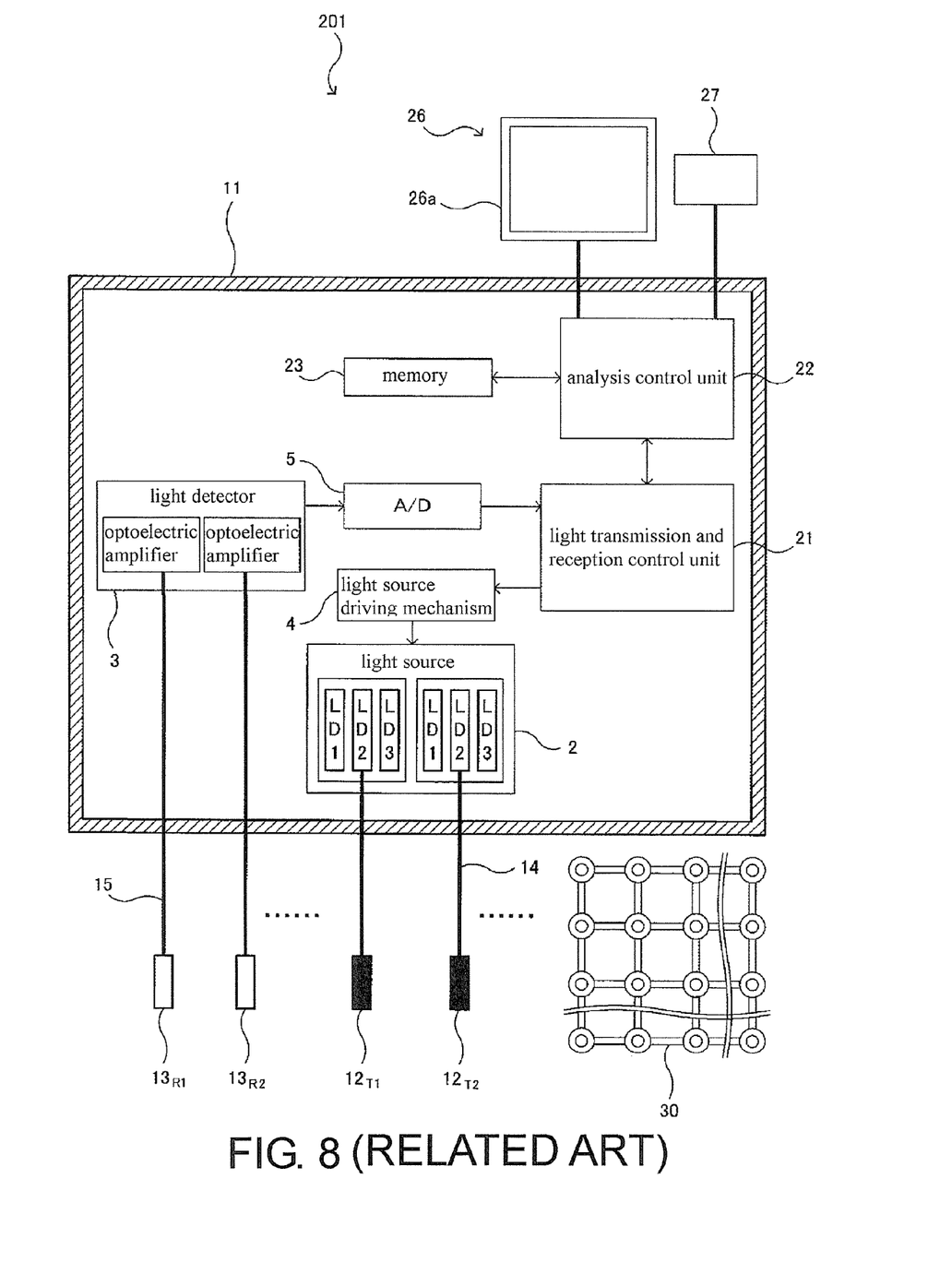
FIG. 8 is a block diagram showing one example of a schematic structure of a conventional near-infrared spectrometer.

FIG. 8 is a block diagram showing one example of a schematic structure of a conventional near-infrared spectrometer. Furthermore, for convenience of viewing, multiple light-transmitting optical fibers and multiple light-receiving optical fibers are omitted.

A near-infrared spectrometer 201 has a housing 11 in rectangular parallelepiped form.

Inside the housing 11, a light source 2 configured to emit light, a light source driving mechanism 4 configured to drive the light source 2, a light detector 3 configured to detect light, an A/D (A/D converter) 5, a light transmission and reception control unit 21, an analysis control unit 22, and a memory 23 are included. In addition, on the outside of the housing 11, sixty-four light-transmitting probes 12, sixty-four light-receiving probes 13, sixty-four light-transmitting optical fibers 14, sixty-four light-receiving optical fibers 15, a display device 26 having a monitor screen 26a or the like, and a keyboard (input device) 27 are included.

The light source driving mechanism 4 drives the light source 2 by a driving signal inputted from the light transmission and reception control unit 21. The light source 2 is, for example, semiconductor lasers LD1, LD2 and LD3 capable of emitting the near-infrared light with three different wavelengths $\lambda 1$, $\lambda 2$ and $\lambda 3$.

The light detector 3 is a detector configured to detect the near-infrared light respectively and thus outputs light reception signals (information on the amount of light received) $A(\lambda 1)$, $A(\lambda 2)$ and $A(\lambda 3)$ to the light transmission and reception control unit 21 via the A/D 5, and is, for example, a photomultiplier or the like.

The light-transmitting optical fiber 14 and the light-receiving optical fiber 15 are in tubular form having a diameter of 2 mm and a length of 2 m~10 m, and are capable of transmitting the near-infrared light along an axial direction so that the near-infrared light entering from one end passes through the inside and exits from another end and that the near-infrared light entering from the another end passes through the inside and exits from the one end.

One light-transmitting optical fiber 14 is connected to one light-transmitting probe 12 and one semiconductor laser LD1, LD2 and LD3 of the light source 2 at two ends so that the two are away from each other at a set length (2 m~10 m).

One light-receiving optical fiber 15 is connected to one light-receiving probe 13 and one photomultiplier of the light detector 3 at two ends so that the two are away from each other at a set length (2 m~10 m).

Figure 9:
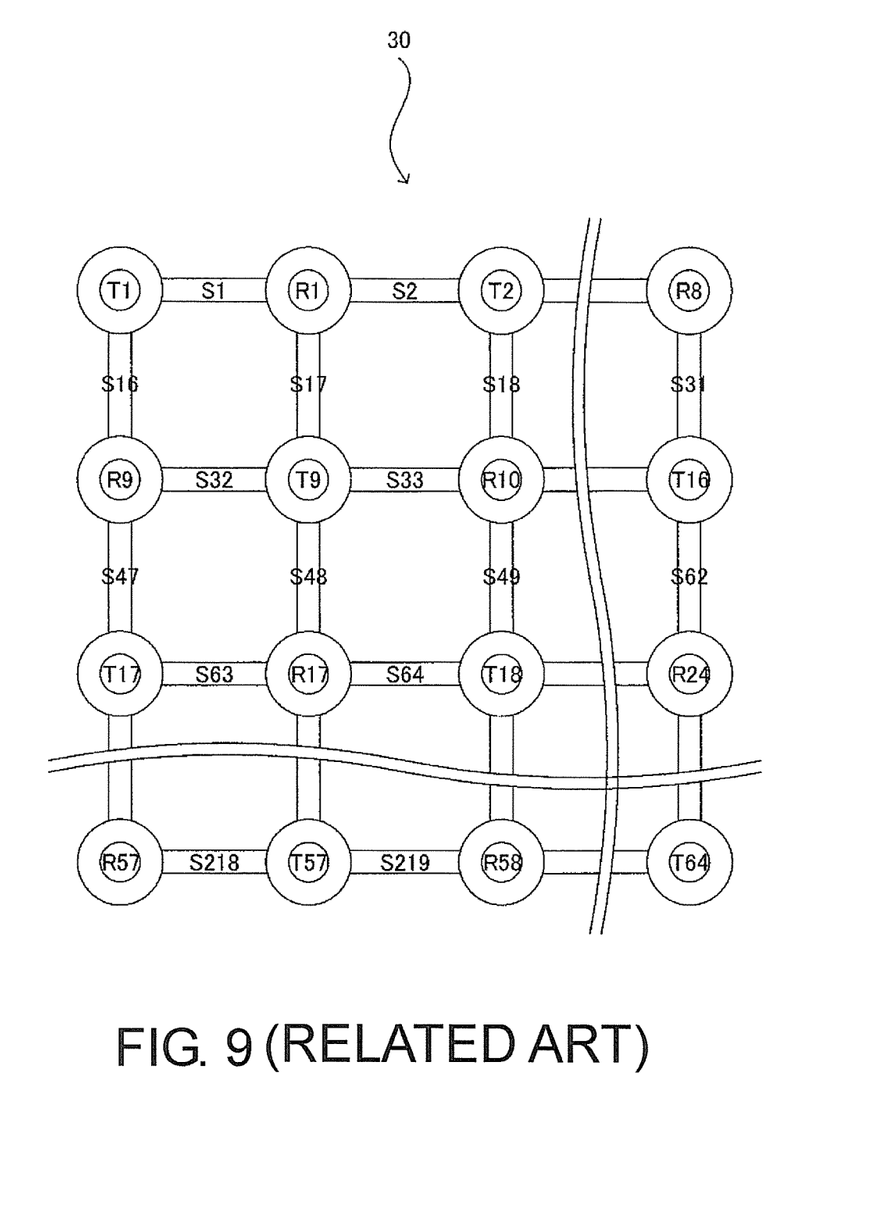
FIG. 9 is a plan diagram showing one example of a holder.

In such near-infrared spectrometer 201, in order to cause the sixty-four light-transmitting probes 12 and the sixty-four light-receiving probes 13 to contact the surface of the subject's head in a predetermined arrangement, a holder 30 is used. FIG. 9 is a plan diagram showing one example of the holder 30 into which sixty-four light-transmitting probes and sixty-four light-receiving probes are inserted.

The light-transmitting probes $12_{T1}$~$12_{T64}$ and the light-receiving probes $13_{R1}$~$13_{R64}$ are alternately arranged with sixteen in the vertical direction and sixteen in the horizontal direction. Accordingly, probe intervals between the light-transmitting probes 12 and the light-receiving probes 13 become constant, and the information on the amount of light received $A(\lambda 1)$, $A(\lambda 2)$ and $A(\lambda 3)$ at a specific depth from the surface of the head is obtained. Furthermore, a channel of 30 mm is generally used, and in the case where the channel is 30 mm, it is considered that the information on the amount of light received $A(\lambda 1)$, $A(\lambda 2)$ and $A(\lambda 3)$ at depths of 15 mm~20 mm from the middle point of the channel may be obtained. That is, a position at depths of 15 mm~20 mm from the surface of the head approximately corresponds to portions on the surface of the brain, and thus, the information on the amount of light received $A(\lambda 1)$, $A(\lambda 2)$ and $A(\lambda 3)$ concerning the brain's activities is obtained.

By the way, in such positional relationship between the sixty-four light-transmitting probes $12_{T1}$~$12_{T64}$ and the sixty-four light-receiving probes $13_{R1}$~$13_{R64}$) is necessary to adjust the timing of irradiating light from the light-transmitting probes 12 and the timing of receiving light by the light-receiving probes 13, so that one light-receiving probe 13 only receives the light irradiated from one light-receiving probe 13, but does not receive the light irradiated from a plurality of light-transmitting probes 12. For this reason, in the memory 23, a control table showing the timing of emitting light by the light source 2 and the timing of detecting light by the light detector 3 is stored.

The light transmission and reception control unit 21, in which such control table is stored in the memory 23, outputs a driving signal configured to transmit light to one light-transmitting probe 12 to the light source driving mechanism 4 at a predetermined time and detects the light reception signals (information on the amount of light received) received by the light-receiving probes 13 using the light detector 3.

As a result, when viewed in a plan view as shown in FIG. 9, collection of a total of 232 pieces (S1~S232) of information on the amount of light received $A(\lambda 1)$, $A(\lambda 2)$ and $A(\lambda 3)$ is carried out.

Then, based on the total of 232 pieces of information on the amount of light received $A(\lambda 1)$, $A(\lambda 2)$ and $A(\lambda 3)$, the analysis control unit 22 calculates the product [oxyHb] of oxyhemoglobin concentration and optical path length, the product [deoxyHb] of deoxyhemoglobin concentration and the optical path length, and the product ([oxyHb]+[deoxyHb]) of the total hemoglobin concentration and optical path length from intensity of passing light of respective wavelengths (absorption wavelength of oxyhemoglobin and absorption wavelength of deoxyhemoglobin) using the relational expressions (1), (2) and (3).

However, to mount the holder 30 as described above on the surface of the subject's head was very time-consuming for a doctor or the like, and was very stressful for the subject to be physically restrained for a long time. In addition, it was very hard for the subject to exercise such as rehabilitation every day.

Figure 3:
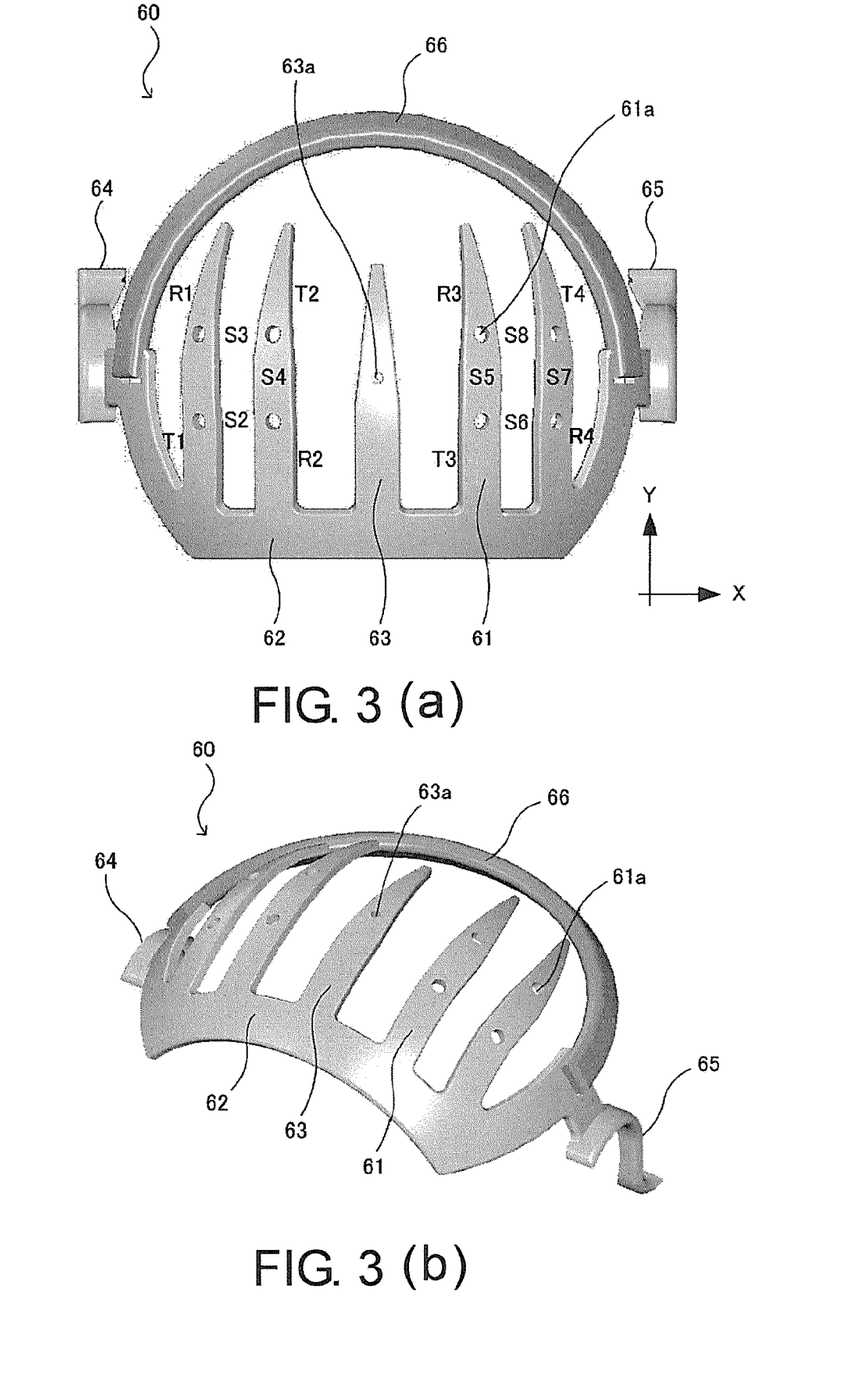
FIGS. 3(a) and 3(b) are diagrams showing one example of an optical bioinstrumentation holder.

Accordingly, the present applicants had previously conceived of a comb-shaped holder to push hair aside by the holder itself so as to enable the subject to exercise such as rehabilitation while mounting the holder on the subject's head in a short time, and had filed patent applications therefor (see Patent Document 2 and Patent Document 3, for example). FIG. 3 is a plan diagram showing one example of the comb-shaped holder. A holder 60 is provided with one linear trunk unit 62 and five linear branches 61 and 63. According to such holder 60, it is possible to mount the holder 60 on the head in a short time.

Meanwhile, a brain wave measurement method has also been known to perform measurements simply and noninvasively inside a living body by using a fact that an electric potential of the surface of the subject's head corresponds to accumulation and summation of electrical activities of nerve cells and synapses. Accordingly, an electroencephalograph (EEG) provided with a holder having a plurality of EEG electrodes and one reference electrode has been developed. In the EEG, potential difference (potential information) is detected by the EEG electrodes arranged on the surface of the subject's head and by the reference electrode arranged in the subject's ears or the like.

Accordingly, the present applicants had previously conceived of a netlike holder capable of executing measurements by an optical bioinstrumentation device and by an EEG at the same time, and filed patent applications therefor (see Patent Document 4, for example).

PRIOR-ART DOCUMENTS

Patent Document

Patent Document 1: Japanese Patent Publication No. 2001-337033
Patent Document 2: International Patent Application No. PCT/JP2010/054628
Patent Document 3: International Patent Application No. PCT/JP2010/062086
Patent Document 4: Japanese Patent Publication No. 2006-223503

Non-Patent Document

Non-Patent Document 1: Factors affecting the accuracy of near-infrared spectroscopy concentration calculations for focal changes in oxygenation parameters, NeuroImage 18, 865-879, 2003

SUMMARY

However, similar to the case of the holder 30, to mount the netlike holder capable of executing measurements by an optical bioinstrumentation device and by an EEG at the same time on the surface of the subject's head was very time-consuming for the doctor or the like, and was very stressful for the subject for being physically restrained for a long time.

Accordingly, although attaching EEG electrodes to the comb-shaped holder 60 for the subject to do exercise such as rehabilitation may also be considered, once the EEG electrodes are attached to the comb-shaped holder 60, the branches 61 of the comb-shaped holder 60 become larger and the number of the branches 61 increases so that the holder 60 itself is not capable of pushing hair aside; as a result, mounting the holder on the head in a short time becomes impossible.

Therefore, the purpose of the invention is to provide a holder set capable of executing measurements by an optical bioinstrumentation device and by an EEG at the same time and of being mounted on the head in a short time, as well as a brain function measuring device using the same.

The holder set of the invention achieved in order to solve the above problems is a holder set provided with an optical bioinstrumentation holder mounted on a subject's head and an EEG holder mounted on the subject's head, the optical bioinstrumentation holder having at least two probe mounting units into which light-transmitting probes configured to irradiate light from a tip or light-receiving probes configured to receive light from a tip are inserted, the EEG holder having at least one electrode mounting unit into which an EEG electrode configured to detect a potential difference with a reference electrode is inserted. The optical bioinstrumentation holder is provided with a linear trunk unit extending in a first direction and at least two linear branches extending in a second direction different from the first direction. The EEG holder is provided with a linear trunk unit extending in the first direction and at least one linear branch extending in a direction opposite to the second direction.

Here, "first direction" and "second direction" are any directions that have been predetermined by the designer of the holder or the like, and it is more preferable that the first direction and the second direction are perpendicular to each other, and for example, the second direction is a front-to rear direction in which it is easy to insert the holder while pushing hair aside.

The optical bioinstrumentation holder related to the holder set of the invention is provided with a linear trunk unit extending in the first direction and at least two linear branches extending in the second direction. That is, the optical bioinstrumentation holder is comb-shaped, which makes it possible for the subject to insert the optical bioinstrumentation holder from the second direction while pushing hair aside using the tip of the branches at the time of mounting the optical bioinstrumentation holder on the head. In addition, the EEG holder related to the holder set of the invention is provided with a linear trunk unit extending in the first direction and at least one linear branches extending in a direction opposite to the second direction. That is, the EEG holder is also comb-shaped. Currently, the EEG holder may also be arranged on the hair since it is for detecting a potential difference. Accordingly, at the time of mounting the EEG holder on the head, the subject will arrange the EEG holder from the above and the rear so as to arrange a branch of the EEG holder between branches of the optical bioinstrumentation holder.

As described above, according to the holder set of the invention, it is possible to mount the optical bioinstrumentation holder and the EEG holder on the subject's head easily in a short time.

Also, the brain function measuring device of the invention may be provided with a holder set as described above, a light-transmitting probe configured to irradiate light on the subject, a light-receiving probe configured to receive light released from the subject, a reference electrode, an EEG electrode configured to detect a potential difference with the reference electrode, a light transmission and reception control unit configured to obtain information on the amount of light received related to the subject's brain activity by controlling the light-transmitting probe to irradiate light on the surface of the head while controlling the light-receiving probe to detect light released from the surface of the head, and an electrode control unit configured to obtain potential information related to the subject's brain activity by controlling the detection of the potential difference between the EEG electrode and the reference electrode.

DESCRIPTION OF THE EMBODIMENTS

In the following, embodiments of the invention are described with reference to the drawings. Furthermore, the invention is not limited to the below-described embodiments, and various modifications are, of course, possible without departing from the gist of the invention.

Figure 1:
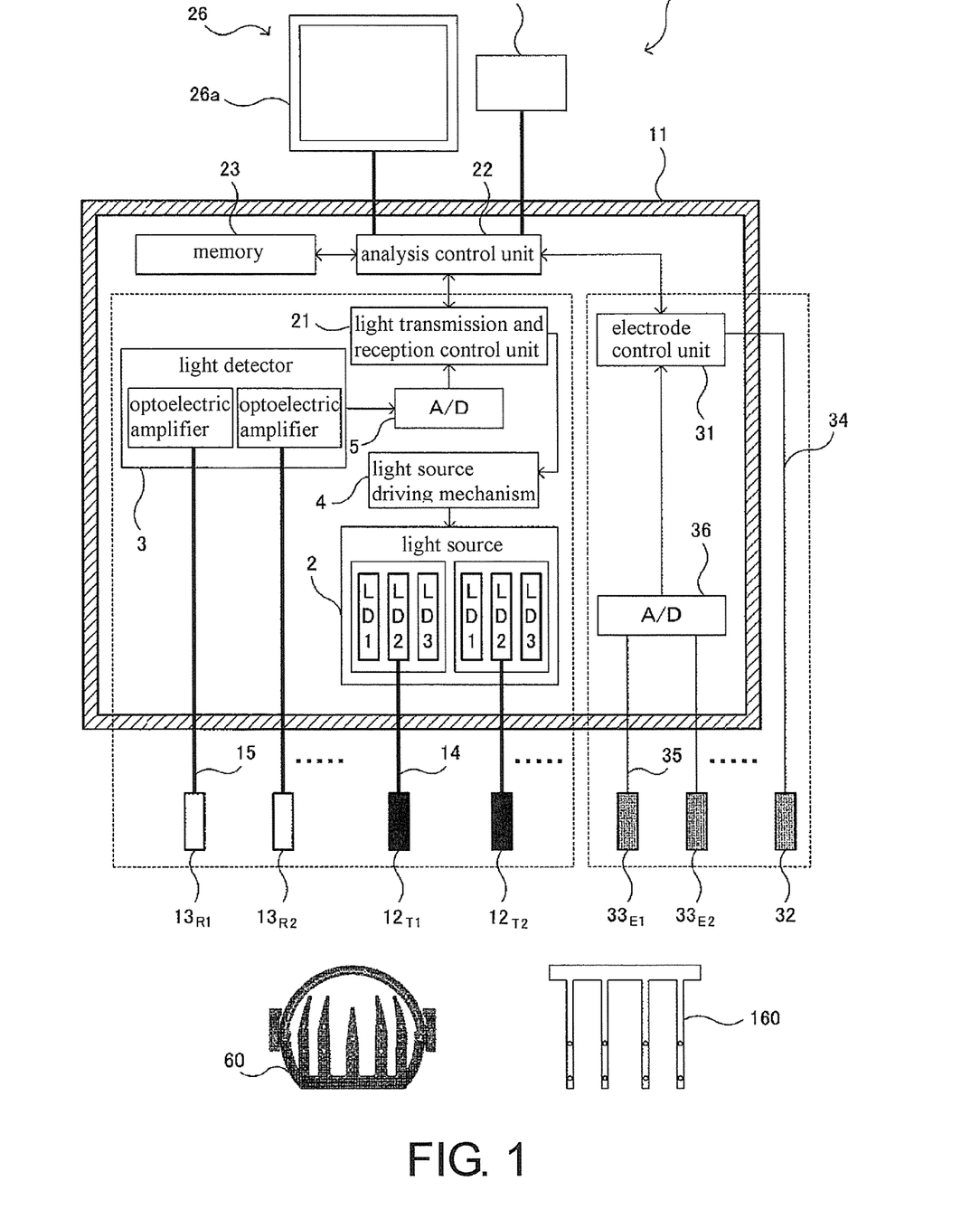
FIG. 1 is a block diagram showing a schematic structure of a brain function measuring device according to one embodiment of the invention.
Figure 2:
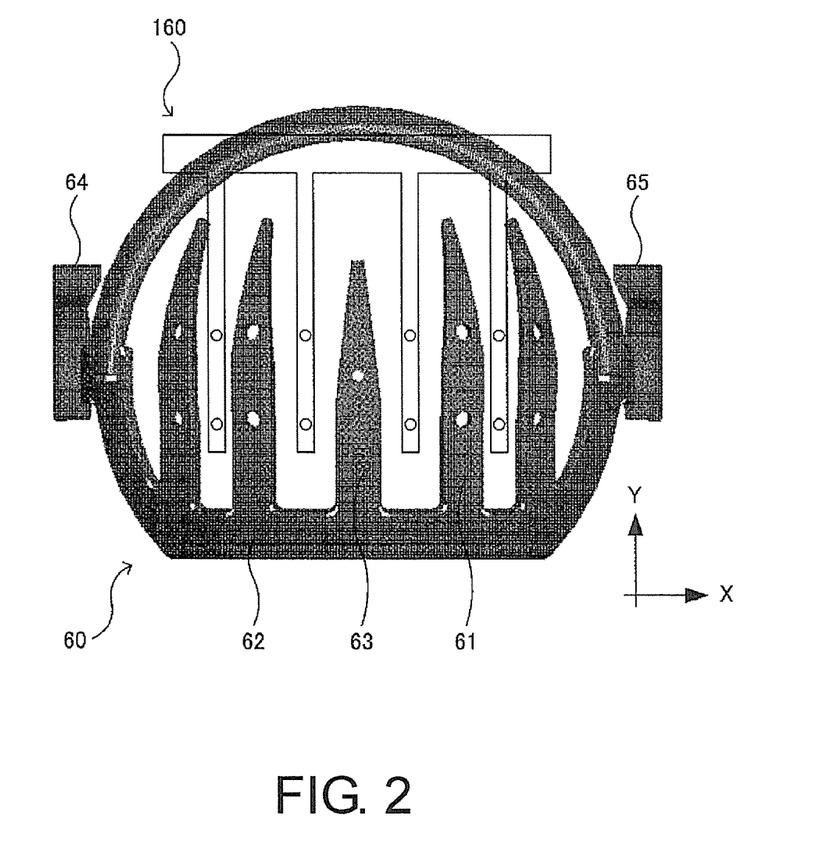
FIG. 2 is a diagram showing one example of a holder set.

FIG. 1 is a block diagram showing a schematic structure of a brain function measuring device according to one embodiment of the invention. In addition, FIG. 2 is a diagram showing one example of a holder set. Furthermore, the same elements as in the near-infrared spectrometer 201 are denoted by the same reference numerals.

A brain function measuring device 1 has a housing 11 in rectangular parallelepiped form as well as a holder set having an optical bioinstrumentation holder 60 and an EEG holder 160 arranged on a surface of a subject's head.

Inside the housing 11, a light source 2 configured to irradiate light, a light source driving mechanism 4 configured to drive the light source 2, a light detector 3 configured to detect light, A/D 5 and 36, a light transmission and reception control unit 21, an electrode control unit 31, an analysis control unit 22, and a memory 23 are provided. In addition, on the outside the housing 11, sixty-four light-transmitting probes 12, sixty-four light-receiving probes 13, sixty-four light-transmitting optical fibers 14, sixty-four light-receiving optical fibers 15, one reference electrode 32, eight EEG electrodes 33, nine wires 34 and 35, a display device 26 having a monitor screen 26a or the like, and a keyboard (input device) 27 are provided.

Here, the optical bioinstrumentation holder 60 is described. FIG. 3(a) is a plan diagram of an optical bioinstrumentation holder, and FIG. 3(b) is an oblique view of the optical bioinstrumentation holder shown in FIG. 3(a).

The optical bioinstrumentation holder 60 is provided with one linear trunk unit 62, four linear first branches 61, one linear second branch 63, a right end 64 to be hooked onto the right ear, a left end 65 to be hooked onto the left ear, and a band 66 for fixing the optical bioinstrumentation holder 60 itself on the head.

The trunk unit 62 extends in an X direction (first direction) in plan view, and is arc-shaped when viewed from the front. The trunk unit 62 has, for example, a width of 15 mm, a thickness of 0.1 mm and a length of 120 mm.

The second branch 63 extends in a Y direction (second direction) perpendicular to the X direction, and has, for example, a width of 15 mm, a thickness of 0.1 mm, and a length of 60 mm. Then, one end of the second branch 63 is connected to a central portion of the trunk unit 62. In addition, another end of the second branch 63 is in tapered form in order to push hair aside.

Furthermore, at a position of 45 mm from the one end of the second branch 63 toward another end, an arrangement reference point 63a being a through hole in circular form (having a diameter of 7 mm, for example) is formed.

Furthermore, in the optical bioinstrumentation holder 60, it is predetermined that a first specific point is the vertex, and thus, the vertex is arranged to be consistent with the arrangement reference point 63a at the time that the optical bioinstrumentation holder 60 is mounted on the head. In addition, at the time that the optical bioinstrumentation holder 60 is mounted on the head, the second branch 63 is arranged to match with a line connecting the vertex and the nasion.

The first branch 61 extends in the Y direction (second direction) perpendicular to the X direction, and has, for example, a width of 15 mm, a thickness of 0.1 mm, and a length of 90 mm. Then, one ends of the first branches 61 are connected to positions of 30 mm and 61.5 mm started from the central portion of the trunk unit 62 in the right direction, and one ends of the first branches 61 are connected to positions of 30 mm and 61.5 mm started from the central portion of the trunk unit 62 in the left direction. In addition, another ends of the first branches 61 are in tapered fruit in order to push the hair aside.

Furthermore, at positions of 30 mm and 61.5 mm from one end toward another end of each first branch 61, through holes (probe mounting units) 61a in circular form (having a diameter of 7 mm) are formed. Accordingly, the through holes 61a form a square with sides of 31.5 mm on the right and left sides of the arrangement reference point 63a.

The light-transmitting probes 12 and the light-receiving probes 13 may be inserted into the inside of the through holes 61a. Accordingly, if the light-transmitting probes $12_{T1}$~$12_{T4}$ and the light-receiving probes $13_{R1}$~$13_{R4}$ are inserted into the through holes 61a of corresponding numbers, when viewed in a plan view as shown in FIG. 3(a), collection of a total of eight pieces (S1~S8) of information on the amount of light received A(λ1), A(λ2) and A(λ3) may be carried out.

The right end 64 is connected to the left end of the trunk unit 62 and may be hooked onto the right ear. In addition, the left end 65 is connected to the right end of the trunk unit 62 and may be hooked onto the left ear.

Material that constitutes such trunk unit 62, first branches 61, second branches 63, right end 64 and left end 65 is not particularly limited, but may include, for example, polypropylene, polyvinyl chloride, polyacetal, metal or the like.

The band 66 is formed to connect the right end with the left end of the trunk unit 62.

Material that constitutes such band 66 is not particularly limited, but may include, for example, rubber having flexibility.

The light-transmitting probes 12 are in columnar form (having a diameter of 5 mm, for example) for enabling the fixing of the probes 12 to the through holes 61a. Then, inside the light-transmitting probes 12, the light-transmitting optical fibers 14 (having a diameter of 2 mm, for example) that have been connected to the light source 2 are fixed via springs or the like so that light is irradiated from a tip of the light-transmitting optical fibers 14.

In addition, the light-receiving probes 13 have the same structure as the light-transmitting probes 12, and are in columnar form (having a diameter of 5 mm, for example) for enabling the fixing of the probes 12 to the through holes 61a. Then, inside the light-receiving probes 13, the light-receiving optical fibers 15 (having a diameter of 2 mm, for example) that have been connected to the light detector 3 are fixed via springs or the like so that light is received by a tip of the light-receiving optical fibers 15.

Figure 4:
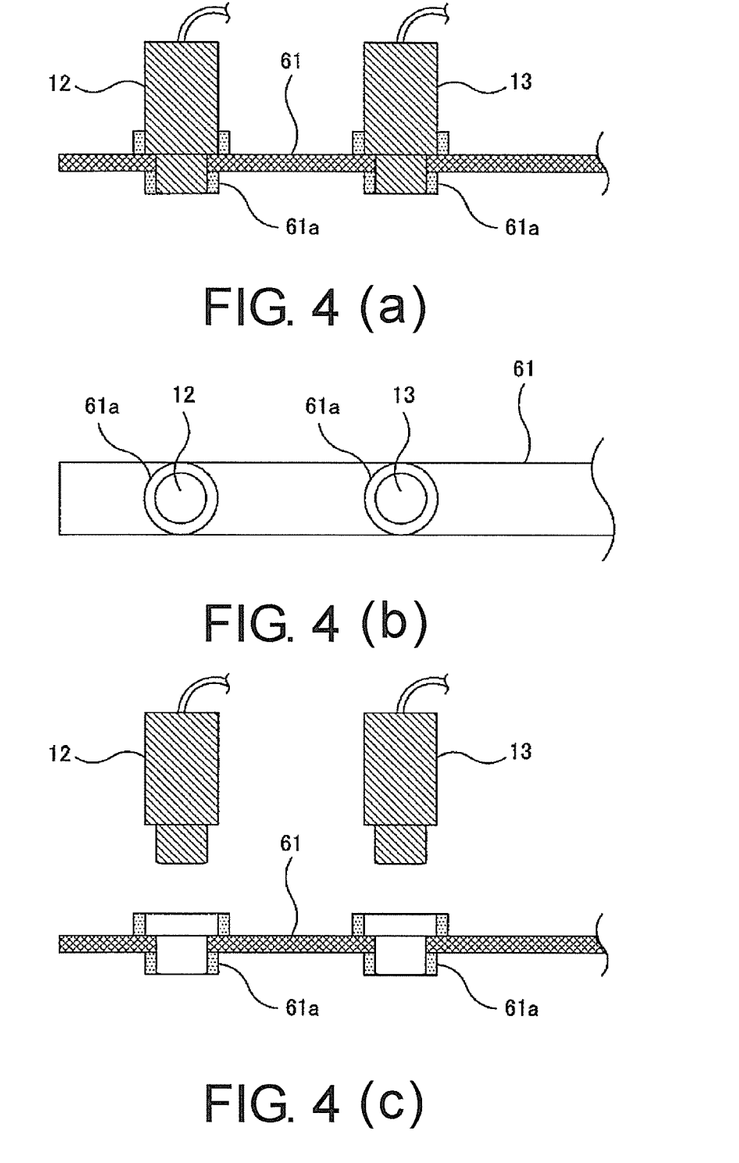
FIGS. 4(a), 4(b) and 4(c) are diagrams showing one example of an optical bioinstrumentation holder.

FIG. 4(a) is a cross-sectional diagram of a portion of the first branch 61 of the optical bioinstrumentation holder 60 to which the light-transmitting probes 12 and the light-receiving probes 13 have been attached. FIG. 4(b) is a rear diagram of the first branch 61 of the optical bioinstrumentation holder 60 shown in FIG. 4(a). FIG. 4(c) is a cross-sectional diagram of a portion of the first branch 61 of the optical bioinstrumentation holder 60 from which the light-transmitting probes 12 and the light-receiving probes 13 have been removed.

Figure 5:
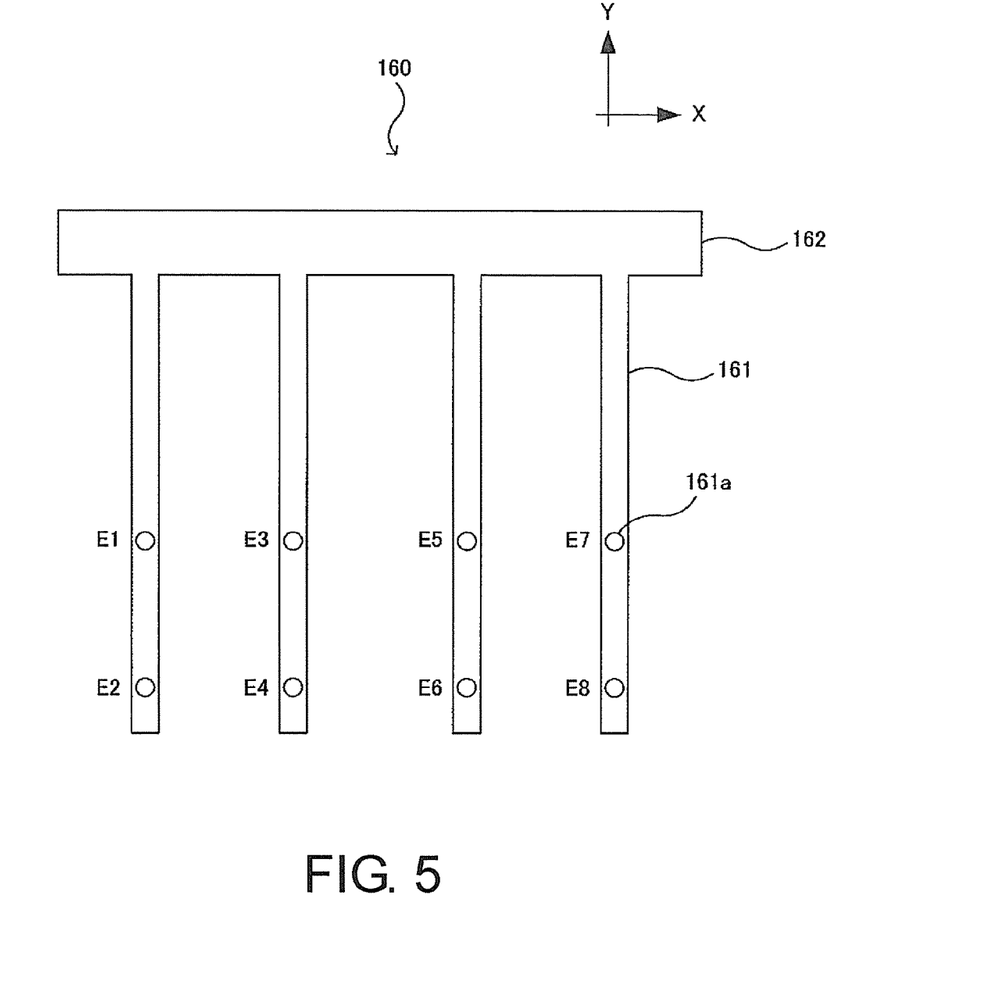
FIG. 5 is a diagram showing one example of an EEG holder.

Next, the EEG holder 160 is described. FIG. 5 is a plan diagram of the EEG holder.

The holder 160 is provided with one linear trunk unit 162 and four linear branches 161.

The trunk unit 162 extends in the X direction (first direction) in plan view, and is arc-shaped when viewed from the front. The trunk unit 162 has, for example, a width of 15 mm, a thickness of 0.1 mm and a length of 120 mm.

The branches 161 extend in a −Y direction (opposite to the second direction) and have, for example, a width of 15 mm, a thickness of 0.1 mm and a length of 90 mm. Then, one ends of the branches 161 are connected to positions of 15 mm and 45 mm started from a central portion of the trunk unit 162 in the right direction, one ends of the branches 161 are connected with positions of 15 mm and 45 mm started from the central portion of the trunk unit 162 in the left direction.

Furthermore, at positions of 30 mm and 61.5 mm from one end toward another end of each branch 161, through holes (probe mounting units) 161a in circular form (having a diameter of 7 mm) are formed. Accordingly, it is possible to arrange the through holes (probe mounting units) 161a between the through holes (probe mounting units) 61a as shown in FIG. 2.

It is possible for the EEG electrodes 33 to be inserted into the inside of the through holes (probe mounting units) 161a. Accordingly, if the EEG electrodes $33_{E1}$~$33_{E8}$ are inserted into the corresponding through holes 161a of the same number, when viewed in a plan view as shown in FIG. 5, collection of a total of eight pieces (E1~E8) of potential information B may be carried out.

Material that constitutes such trunk unit 162 and branch 161 is not particularly limited, but may include, for example, polypropylene, polyvinyl chloride, polyacetal, metal or the like.

One reference electrode 32 is fixed to the subject's ear or the like.

The EEG electrodes 33 are in columnar form (having a diameter of 5 mm, for example) for enabling the fixing of the probes 12 to the through holes 161a, and are configured to detect a potential difference with the reference electrode 32. Then, the wires 35 (having a diameter of 1 mm, for example) are fixed to the ends of the EEG electrodes 33 and connected to the electrode control unit 31 via the A/D 36. Currently, one EEG electrode 33 and the A/D 36 are connected to two ends of one wire 35, and thus separated from each other by a set length (2 m~10 m). Accordingly, eight EEG electrodes 33 respectively output detection signals (potential information) to the electrode control unit 31.

Figure 6:
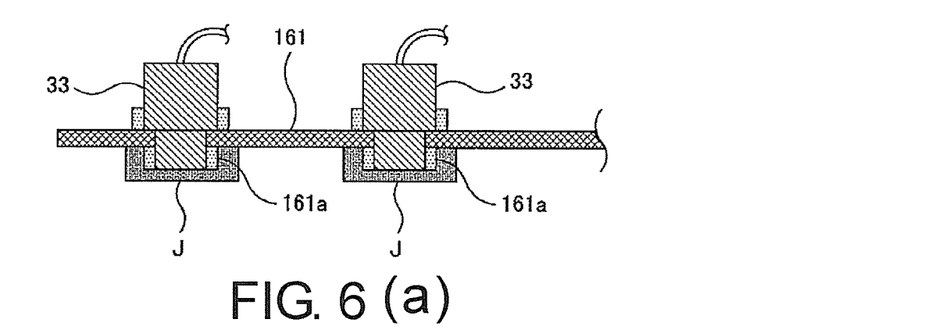
FIGS. 6(a), 6(b) and 6(c) are diagrams showing one example of an EEG holder.

FIG. 6(a) is a cross-sectional diagram of a portion of the branch 161 of the EEG holder 160 to which the EEG electrodes 33 have been attached. FIG. 6(b) is a diagram illustrating the rear view of the branch 161 of the EEG holder 160 shown in FIG. 6(a). FIG. 6(c) is a cross-sectional diagram of a portion of the branch 161 of the EEG holder 160 from which the EEG electrodes 33 have been removed.

According to such brain function measuring device 1, firstly, the subject and the doctor or the like insert the light-transmitting probes $12_{T1}$~$12_{T4}$ and the light-receiving probes $13_{R1}$~$13_{R4}$ into the through holes 61a of the optical bioinstrumentation holder 60 in a predetermined arrangement. Next, the subject and the doctor or the like arrange the optical bioinstrumentation holder 60 on the head to insert the optical bioinstrumentation holder 60 from the front toward the rear of the head while pushing the hair aside. Then, the subject and the doctor or the like make arrangements so that the vertex matches the arrangement reference point 63a, and the second branch 63 is matched with the line connecting the vertex and the nasion. Furthermore, the holder 60 is fixed to the head by the right end 64, the left end 65 and the band 66.

Next, the doctor or the like arranges the EEG holder 160 on the head from the above and the rear of the head. Currently, the doctor or the like arranges the through holes (probe mounting units) 161a between the through holes (probe mounting units) 61a as shown in FIG. 2. After that, the doctor or the like inserts the EEG electrodes 33 into the through holes 161a of the EEG holder 160 in a predetermined arrangement after wetting the through holes 161a and the head near the through holes 161a with gel J.

As described above, according to the brain function measuring device 1 of the invention, it is possible to mount the optical bioinstrumentation holder 60 and the EEG holder 160 on the subject's head easily in a short time.

OTHER EMBODIMENTS (1) The above-described brain function measuring device 1 has a structure where the optical bioinstrumentation holder 60 is mounted on the head from the front toward the rear of the head, but it may also have a structure where the optical bioinstrumentation holder is mounted on the head from the right side toward the left side of the head.

(2) The above-described brain function measuring device 1 includes a structure where four light-transmitting probes $12_{T1}$~$12_{T4}$ and four light-receiving probes $13_{R1}$~$13_{R4}$ are attached to the optical bioinstrumentation holder 60, but it may also have a structure where eight light-transmitting probes and eight light-receiving probes are attached to the optical bioinstrumentation holder, or a structure where two light-transmitting probes and two light-receiving probes are attached to the optical bioinstrumentation holder. In addition, it has a structure where eight EEG electrodes $33_{E1}$~$33_{E8}$ are attached to the EEG holder 160, but it may also have a structure where four EEG electrodes are attached to the EEG holder, or a structure where two EEG electrodes are attached to the EEG holder.

(3) The above-described brain function measuring device 1 has a structure where an optical bioinstrumentation device and an EEG are integrally provided, but it may also have a structure where an optical bioinstrumentation device and an EEG are separated.

The invention may be applied to brain function measuring devices or the like capable of executing measurements by an optical bioinstrumentation device and by an EEG at the same time.

What is claimed is:

1. A brain function measuring device, comprising:
an optical bioinstrumentation holder, configured to be mounted on a subject's head, comprising a first linear trunk unit and a plurality of first linear branches to be comb-shaped, and having, a plurality of probe mounting units, wherein the probe mounting units are configured to hold light-transmitting probes for irradiating light from a tip thereof or light-receiving probes for receiving light from a tip thereof;
an electroencephalograph holder, configured to be mounted on the subject's head, comprising a second linear trunk unit and a plurality of second linear branches to be comb-shaped, and having a plurality of electrode mounting units, wherein the electrode mounting units are configured to hold electroencephalography electrodes for detecting a potential difference with a reference electrode;
the light-transmitting probes configured to irradiate the light on the subject;
the light-receiving probes configured to receive the light released from the subject;
the reference electrode;
the electroencephalography electrodes configured to detect the potential difference with the reference electrode;
a light transmission and reception control unit configured to obtain information on an amount of the light received related to the subject's brain activity by controlling the light-transmitting probes to irradiate the light on a surface of a head while controlling the light-receiving probes to detect the light released from the surface of the head; and
an electrode control unit configured to obtain potential difference information related to the subject's brain activity by controlling the detection of the potential difference between the electroencephalography electrodes and the reference electrode.

* * * * *